(12) United States Patent
Miller et al.

(10) Patent No.: US 8,469,873 B2
(45) Date of Patent: *Jun. 25, 2013

(54) BLOOD VESSEL WRAP

(75) Inventors: Scott H Miller, Manly (AU); William Suttle Peters, Auckland (NZ); Gemma De Plater, Waverton (AU)

(73) Assignee: Sunshine Heart Company Pty Ltd, Eden Prairie, MN (US)

( * ) Notice: Subject to any disclaimer, the term of this patent is extended or adjusted under 35 U.S.C. 154(b) by 161 days.

This patent is subject to a terminal disclaimer.

(21) Appl. No.: 12/962,327

(22) Filed: Dec. 7, 2010

(65) Prior Publication Data

US 2011/0196467 A1  Aug. 11, 2011

Related U.S. Application Data

(63) Continuation of application No. 10/595,602, filed as application No. PCT/AU2004/001484 on Oct. 28, 2004, now Pat. No. 7,862,499.

(51) Int. Cl.
*A61N 1/362* (2006.01)

(52) U.S. Cl.
USPC ............................................. 600/16; 602/44

(58) Field of Classification Search
USPC ............. 600/16, 17; 602/42–44, 53; 606/157, 606/158
See application file for complete search history.

(56) References Cited

U.S. PATENT DOCUMENTS

| | | | |
|---|---|---|---|
| 283,660 A | 8/1883 | Reed | |
| 929,571 A | 7/1909 | Dubied | |
| 1,576,397 A | 3/1926 | Yanagi | |
| 1,719,316 A | 7/1929 | Appleton | |
| 3,467,077 A | 9/1969 | Cohen | |
| 3,552,383 A | 1/1971 | Krueger et al. | |
| 3,597,766 A | 8/1971 | Buck | |
| 4,014,318 A | 3/1977 | Dockum et al. | |

(Continued)

FOREIGN PATENT DOCUMENTS

| | | |
|---|---|---|
| AU | 2003277983 B2 | 6/2008 |
| DE | 1541311 A1 | 9/1969 |

(Continued)

OTHER PUBLICATIONS

Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ASAIO, Hagerstown, MD, May 1, 1996.

(Continued)

*Primary Examiner* — Brian T Gedeon
(74) *Attorney, Agent, or Firm* — Davis, Brown, Koehn, Shors & Roberts, P.C.; Sean D. Solberg

(57) ABSTRACT

A wrap (20) for securing about a blood vessel (36) by encasing a section of the vessel. The wrap (20) being of thin flexible construction having two ends (22, 24) and two sides (26, 28). The wrap (20) is more elastic or stretchable at, near, or along at least some of its sides (22, 24) compared to at, near, or along its centre, to provide strain relief from wrapped to unwrapped aorta. The wrap (20) is not inelastic, so that loss of aortic compliance is minimised or enhanced. The wrap (20) is adapted to apply, in use, less compressive force at, near, or along at least some of its sides (22, 24) compared to at, near, or along its centre.

20 Claims, 4 Drawing Sheets

U.S. PATENT DOCUMENTS

| | | | |
|---|---|---|---|
| 4,046,137 A | 9/1977 | Curless et al. |
| 4,051,840 A | 10/1977 | Kantrowitz et al. |
| 4,176,411 A | 12/1979 | Runge |
| 4,195,623 A | 4/1980 | Zeff et al. |
| 4,236,482 A | 12/1980 | Gingerich et al. |
| 4,256,094 A | 3/1981 | Kapp et al. |
| 4,277,706 A | 7/1981 | Isaacson |
| 4,304,225 A | 12/1981 | Freeman |
| 4,454,891 A | 6/1984 | Dreibelbis et al. |
| 4,457,673 A | 7/1984 | Conley et al. |
| 4,459,977 A | 7/1984 | Pizon et al. |
| 4,515,587 A | 5/1985 | Schiff |
| 4,583,523 A | 4/1986 | Kleinke et al. |
| 4,594,731 A | 6/1986 | Lewkowicz |
| 4,630,597 A | 12/1986 | Kantrowitz et al. |
| 4,676,482 A | 6/1987 | Reece et al. |
| 4,697,574 A | 10/1987 | Karcher et al. |
| 4,763,646 A | 8/1988 | Lekholm |
| 4,771,765 A | 9/1988 | Choy et al. |
| 4,809,676 A | 3/1989 | Freeman |
| 4,813,952 A | 3/1989 | Khalafalla |
| 4,822,357 A | 4/1989 | Forster et al. |
| 4,881,939 A | 11/1989 | Newman |
| 4,886,490 A | 12/1989 | Shiber |
| 4,957,477 A | 9/1990 | Lundback |
| 4,979,936 A | 12/1990 | Stephenson et al. |
| 5,089,017 A | 2/1992 | Young et al. |
| 5,169,378 A | 12/1992 | Figuera |
| 5,197,980 A | 3/1993 | Gorshkov et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee et al. |
| 5,290,249 A | 3/1994 | Foster et al. |
| 5,300,111 A | 4/1994 | Panton et al. |
| 5,337,752 A | 8/1994 | Reeves |
| 5,344,385 A | 9/1994 | Buck et al. |
| 5,360,445 A | 11/1994 | Goldowsky |
| 5,372,573 A | 12/1994 | Habib |
| 5,429,584 A | 7/1995 | Chiu |
| 5,447,523 A | 9/1995 | Schaldach |
| 5,453,076 A | 9/1995 | Kiyota et al. |
| 5,511,551 A | 4/1996 | Sano et al. |
| 5,554,177 A | 9/1996 | Kieval et al. |
| 5,569,156 A | 10/1996 | Mussivand |
| 5,593,414 A | 1/1997 | Shipp et al. |
| 5,607,378 A | 3/1997 | Winston |
| 5,647,380 A | 7/1997 | Campbell et al. |
| 5,722,930 A | 3/1998 | Larson, Jr. et al. |
| 5,792,195 A | 8/1998 | Carlson et al. |
| 5,814,012 A | 9/1998 | Fleenor et al. |
| 5,820,542 A | 10/1998 | Dobak, III et al. |
| 5,827,171 A | 10/1998 | Dobak, III et al. |
| 5,843,170 A | 12/1998 | Ahn |
| 5,975,140 A | 11/1999 | Lin |
| 5,980,488 A | 11/1999 | Thorne |
| 6,030,336 A | 2/2000 | Franchi |
| 6,045,496 A | 4/2000 | Pacella et al. |
| 6,066,085 A | 5/2000 | Heilman et al. |
| 6,066,086 A | 5/2000 | Antaki et al. |
| 6,132,363 A | 10/2000 | Freed et al. |
| 6,132,636 A | 10/2000 | Singh et al. |
| 6,210,318 B1 | 4/2001 | Lederman |
| 6,210,319 B1 | 4/2001 | Williams et al. |
| 6,226,843 B1 | 5/2001 | Crainich |
| 6,251,061 B1 | 6/2001 | Hastings et al. |
| 6,406,422 B1 | 6/2002 | Landesberg |
| 6,432,039 B1 | 8/2002 | Wardle |
| 6,471,633 B1 | 10/2002 | Freed |
| 6,553,263 B1 | 4/2003 | Meadows et al. |
| 6,572,534 B1 | 6/2003 | Milbocker et al. |
| 6,585,635 B1 | 7/2003 | Aldrich |
| 6,616,596 B1 | 9/2003 | Milbocker |
| 6,626,821 B1 | 9/2003 | Kung et al. |
| 6,643,548 B1 | 11/2003 | Mai et al. |
| 6,808,483 B1 | 10/2004 | Ortiz et al. |
| 6,808,484 B1 | 10/2004 | Peters et al. |
| 6,984,201 B2 | 1/2006 | Khaghani et al. |
| 7,169,109 B2 | 1/2007 | Jansen et al. |
| 7,347,811 B2 | 3/2008 | Peters et al. |
| 7,357,771 B2 | 4/2008 | Peters et al. |
| 7,360,558 B1 | 4/2008 | Chen et al. |
| 7,513,864 B2 | 4/2009 | Kantrowitz et al. |
| 7,740,575 B2 | 6/2010 | Peters et al. |
| 7,765,003 B2 | 7/2010 | Peters et al. |
| 2001/0016676 A1 | 8/2001 | Williams et al. |
| 2003/0105497 A1 | 6/2003 | Zhu et al. |
| 2004/0010180 A1 | 1/2004 | Scorvo |
| 2004/0073080 A1 | 4/2004 | Peters et al. |
| 2004/0097783 A1 | 5/2004 | Peters et al. |
| 2004/0097784 A1 | 5/2004 | Peters et al. |
| 2004/0147803 A1 | 7/2004 | Hegde et al. |
| 2004/0152945 A1 | 8/2004 | Kantrowitz et al. |
| 2006/0052866 A1 | 3/2006 | Gilles et al. |
| 2007/0021830 A1 | 1/2007 | Peters et al. |
| 2007/0093684 A1 | 4/2007 | Peters et al. |
| 2007/0129796 A1 | 6/2007 | Miller et al. |
| 2007/0135677 A1 | 6/2007 | Miller et al. |
| 2007/0167898 A1 | 7/2007 | Peters et al. |
| 2008/0027270 A1 | 1/2008 | Peters et al. |
| 2008/0139873 A1 | 6/2008 | Peters et al. |
| 2008/0167515 A1 | 7/2008 | Peters et al. |
| 2008/0194905 A1 | 8/2008 | Walsh |
| 2010/0292528 A1 | 11/2010 | De Plater et al. |
| 2010/0324354 A1 | 12/2010 | Peters et al. |
| 2011/0270331 A1 | 11/2011 | Peters et al. |
| 2011/0275883 A1 | 11/2011 | Peters |
| 2011/0288367 A1 | 11/2011 | Miller |

FOREIGN PATENT DOCUMENTS

| | | |
|---|---|---|
| EP | 0080348 B1 | 5/1988 |
| EP | 0363203 A2 | 4/1990 |
| EP | 0216042 B1 | 3/1991 |
| EP | 0601804 A1 | 6/1994 |
| EP | 0364799 A2 | 5/1995 |
| EP | 1129736 A1 | 9/2001 |
| FR | 2458288 A1 | 1/1981 |
| FR | 2645739 A1 | 10/1990 |
| FR | 2767874 A1 | 3/1999 |
| GB | 2422114 B | 4/2008 |
| JP | 6510461 A | 11/1994 |
| JP | 9502376 A | 3/1997 |
| JP | 9503933 A | 4/1997 |
| JP | 10328297 A | 12/1998 |
| JP | 11285529 A | 10/1999 |
| JP | 2000000299 A | 1/2000 |
| JP | 2000510006 T | 8/2000 |
| JP | 2001276213 A | 10/2001 |
| JP | 2003135497 A | 5/2003 |
| WO | WO9015630 A1 | 12/1990 |
| WO | WO9208500 A1 | 5/1992 |
| WO | WO9308874 A1 | 5/1993 |
| WO | WO9505122 A1 | 2/1995 |
| WO | WO9528127 A1 | 10/1995 |
| WO | WO9740755 A1 | 11/1997 |
| WO | WO9805289 A1 | 2/1998 |
| WO | WO9814239 A1 | 4/1998 |
| WO | WO9851367 A1 | 11/1998 |
| WO | WO9902213 A1 | 1/1999 |
| WO | WO9904833 A1 | 2/1999 |
| WO | WO9945981 A1 | 9/1999 |
| WO | WO0012168 A1 | 3/2000 |
| WO | WO0076288 A2 | 12/2000 |
| WO | WO0113974 A2 | 3/2001 |
| WO | WO0183001 A1 | 11/2001 |
| WO | WO0224254 A2 | 3/2002 |
| WO | WO0224255 A1 | 3/2002 |
| WO | WO02076305 A1 | 10/2002 |
| WO | WO03011365 A1 | 2/2003 |
| WO | WO03028787 A1 | 4/2003 |
| WO | WO2004045677 A1 | 6/2004 |
| WO | WO2005041783 A1 | 5/2005 |
| WO | WO2005042063 A1 | 5/2005 |
| WO | WO2005044338 A1 | 5/2005 |
| WO | WO2005110512 A1 | 11/2005 |
| WO | WO2008053469 A2 | 5/2008 |
| WO | WO2008071223 A1 | 6/2008 |

OTHER PUBLICATIONS

International Preliminary Examination Report issued in PCT/AU2001/01187, completed May 2, 2002, 4 pages.
International Preliminary Examination Report issued in PCT/AU2002/000974, completed Aug. 11, 2003, 8 pages.
International Preliminary Examination Report issued in PCT/AU2003/001450, completed Mar. 2, 2005, 4 pages.
International Preliminary Report on patentability, Chapter II, issued in PCT/AU2007/001188, completed Mar. 11, 2008, 8 pages.
International Prelminary Examination Report issued in PCT/AU2003/001458, completed Mar. 7, 2005, 7 pages.
International Search Report and Written Opinion issued in PCT/AU2004/001483, mailed Nov. 26, 2004, 5 pages.
International Search Report and Written Opinion issued in PCT/AU2004/001484, mailed Nov. 29, 2004, 5 pages.
International Search Report and Written Opinion issued in PCT/AU2004/001486, mailed Jan. 6, 2005, 7 pages.
International Search Report and Written Opinion issued in PCT/AU2004/01485, mailed Feb. 7, 2005, 6 pages.
International Search Report and Written Opinion issued in PCT/AU2004/01487, mailed Jan. 27, 2005, 12 pages.
International Search Report and Written Opinion issued in PCT/AU2004/01488, mailed Dec. 15, 2004, 6 pages.
International Search Report and Written Opinion issued in PCT/AU2007/001188, mailed Oct. 4, 2007, 12 pages.
International Search Report issued in PCT/AU00/00654, mailed Aug. 18, 2000, 5 pages.
International Search Report issued in PCT/AU2001/01187, mailed Nov. 5, 2001, 3 pages.
International Search Report issued in PCT/AU2002/000974, mailed Oct. 11, 2002, 5 pages.
International Search Report issued in PCT/AU2003/001450, mailed Feb. 2, 2004, 2 pages.
International Search Report issued in PCT/AU2003/001458, mailed Feb. 5, 2004, 5 pages.
J.L. Stewart, "Aortic Cuff a Cardiac Assistance Device", Polytechnic Institute of Brooklyn, 1968, pp. 9-108.
Luisada et al., On the Function of the Aortic Valve and the Mechanism of the First and Second Sounds, Japanese Heart Journal, vol. 18(1), Jan. 1977, pp. 81-91.
Office Action issued in JP Application No. 2004-552261, dated Mar. 2, 2010.
Office Action issued in JP Application No. 22006-53700, dispatched Jun. 22, 2010, with English translation, 12 pages.
Seymour Furman et al., "Cardiac Support by Periaortic Diastolic Augmentation", New York Journal of Medicine, Aug. 1, 1970, pp. 1964-1969.
Supplemental European Search Report issued in EP 01971489, completed Nov. 22, 2006, 4 pages.
Supplemental European Search Report issued in EP 04789625, mailed Nov. 18, 2009, 6 pages.
Supplemental European Search Report issued in EP App No. 02748447, Feb. 6, 2007, 6 pages.
Supplemental European Search Report issued in EP App. No. 04789624, mailed Mar. 6, 2008, 7 pages.
Supplemental European Search Report issued in EP Application 00934813, mailed Oct. 19, 2006, 2 pages.
Use of Heart Valve Sounds as Input to Cardiac Assist Devices, Research Disclosures, Mar. 1995.

BLOOD VESSEL WRAP

CROSS-REFERENCE TO RELATED APPLICATION

This application is a continuation of U.S. patent application Ser. No. 10/595,602, filed Feb. 22, 2007, which is the U.S. national stage of PCT Application PCT/AU2004/001484, filed Oct. 28, 2004, which claims priority to Australian Provisional Application AU20030905992, filed Oct. 30, 2003, all of which are hereby incorporated herein by reference in its entirety.

TECHNICAL FIELD

The present invention relates to a wrap for securing about a blood vessel, and in particular for holding a vessel deformer adjacent an arterial vessel.

The invention has been primarily developed for use in securing the inflatable balloon or chamber of an implantable counter-pulsation heart assist device against the ascending aorta and will be described hereinafter with reference to this application.

BACKGROUND

The Applicant's International PCT Patent Application Nos. PCT/AU00/00654 and PCT/AU01/01187 disclose heart assist devices, systems and methods. More particularly, these specifications disclose vessel deformers in the form of inflatable balloon or chambers which form part of implantable counter-pulsation heart assist devices. The balloon or chambers are cyclically inflated and deflated and used to compress the patient's ascending aorta during diastole and release the compression during systole.

The balloon or chamber are generally secured to the aorta by a substantially non-elastic wrap or sheath, which is secured around a section of the aorta with the balloon or chamber therebetween. For the heart assist device to function efficiently, it is necessary that the wrap be a snug fit around the aorta when the balloon or chamber is deflated.

Hitherto, wraps have been manufactured from a length of substantially inflexible woven polyester material. The disadvantage of known wraps will be described with reference to FIG. 3 which shows a section of aorta 10 encased by a known wrap 12. If the wrap 12 is over-tightened (as shown), its sides cause a sharp depression or kink in the aorta 10, in the regions indicated by the reference numeral 14. This can also occur due to the aorta 10 enlarging slightly as the patient recovers or with age. This depression/kinking places a higher strain on the wall of the aorta 10 and can damage same. Also, the kink in the internal wall of the aorta 10 induces turbulence in the blood flow, which increases the likelihood of plaque formation.

Wrapping a curved vessel with a flat straight piece of fabric also leads to bunching or folding of the fabric. This is undesirable as it encourages secondary growth or potential infection in the bunched/folded region and results in uneven load distribution.

It is also known to place static wraps around blood vessels, for instance to reinforce vessels suffering from aneurysmal disease.

Any aortic compliance may be lost by placement of non-elastic or non shape-changing wrap, which may reduce the natural advantage of aortic compliance on cardiac function.

It is an object of the present invention to provide a wrap that substantially overcome or at least ameliorate one or more of the above disadvantages.

SUMMARY

Accordingly, in a first aspect, the present invention provides a wrap for securing about a blood vessel by encasing a section of the vessel, the wrap being of thin flexible construction having two ends and two sides. It is preferable that the wrap is more elastic or stretchable at, near, or along at least some of its sides compared to at, near, or along its centre, to provide strain relief from wrapped to unwrapped aorta.

It is preferable that the wrap is not inelastic, and that loss of aortic compliance is minimized, or in fact enhanced.

In a second aspect, the present invention provides a wrap for securing about a blood vessel by encasing a section of the vessel, the wrap being of thin flexible construction having two ends and two sides and being adapted to apply, in use, less compressive force at, near, or along at least some of its sides compared to at, near, or along its centre.

The wrap is preferably adapted for securing a vessel deformer adjacent the vessel, by sandwiching the deformer between the vessel and the wrap. The vessel deformer is preferably part of an implantable counter-pulsation heart assist device and most preferably is in the form of an inflatable balloon or chamber. The wrap is preferably adapted to secure the inflatable balloon or chamber against an aorta, most preferably the ascending aorta.

The wrap is preferably of woven or knitted construction, or a combination, and made of material such as polyester or PET (polyethylene terepthalate).

In one form, the wrap has slits along some of its sides, most preferably a series of spaced part slits that are normal to the direction of the sides. The slits make those parts of the sides more elastic or stretchable than the centre of the wrap.

In another form, the wrap has warp fibres at, near, or along its sides that are more elastic than the warp fibres at, near, or along its centre. In this form, the warp fibres, near or along its sides are preferably crimped and the warp fibres at, near, or along its centre are preferably un-crimped or less crimped.

In another form, the wrap includes a strip of substantially centrally placed material, that has a tensile strength greater than that of the rest of the wrap.

In another form, the woven fabric may be cut on the bias to allow a more conformal wrap and with some improved elasticity along the edge areas of the wrap.

The two sides of the wrap can be of similar, or differing, elasticity or stretchability to each other. In the case of differing, the more elastic or stretchable side is positioned closer to the heart, as this is where there is greater movement.

In a yet further form, the wrap is thinner at, near, or along its sides compared to at, near, or along its centre.

The wrap is preferably about six times longer than it is wide, most preferably with a slimmed region at or near its longitudinal midpoint. The wrap desirably includes one or more, preferably two, longitudinal slits near its thinned region to allow the wrap to conform radially more closely with the inner curve of the aorta. The wrap is preferably shaped to allow good conformance with the curved aorta—the slits allow improved conformity. The wrap preferably also includes an opening for a fluid tube.

In another embodiment, the wrap may be coated with a material to reduce its surface area and to limit tissue ingrowth.

The wrap is preferably coated on one or both sides with either silicone or polyurethane or a co-polymer of both.

BRIEF DESCRIPTION OF THE DRAWINGS

Preferred embodiments of the present invention will now be described, by way of examples only, with reference to the accompanying drawings in which.

DETAILED DESCRIPTION

Figure 1:
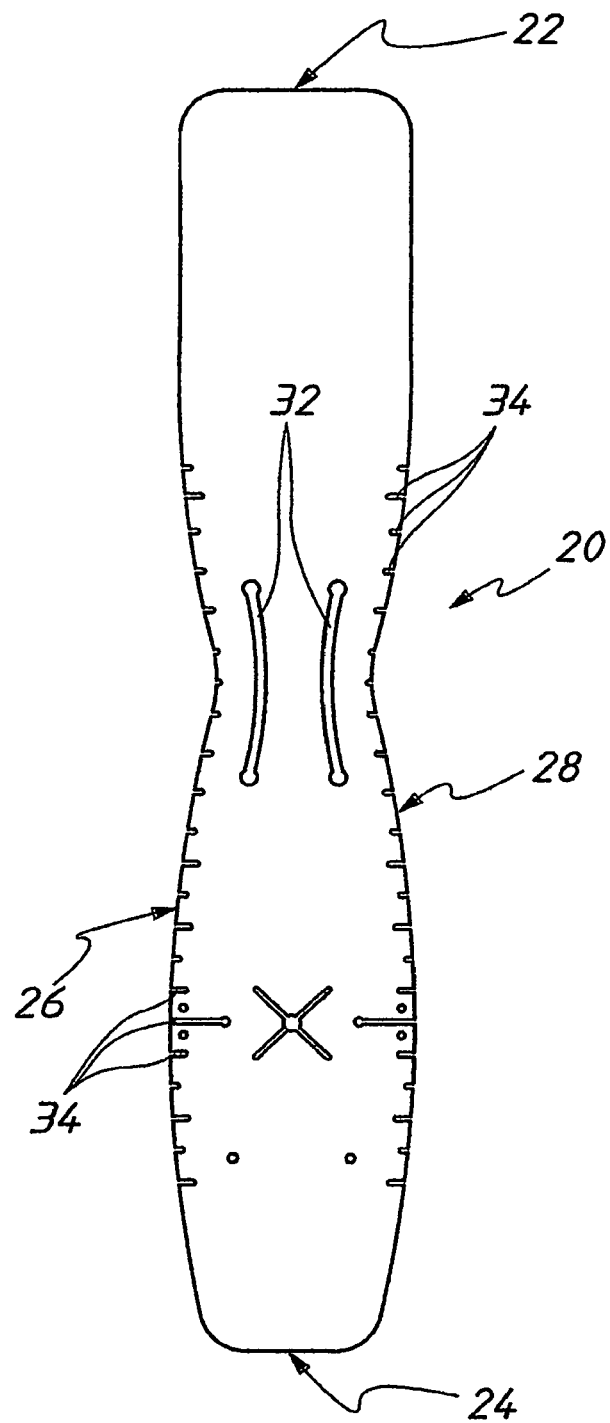
FIG. 1 is a top view of a first embodiment of a wrap according to the invention.
Figure 2:
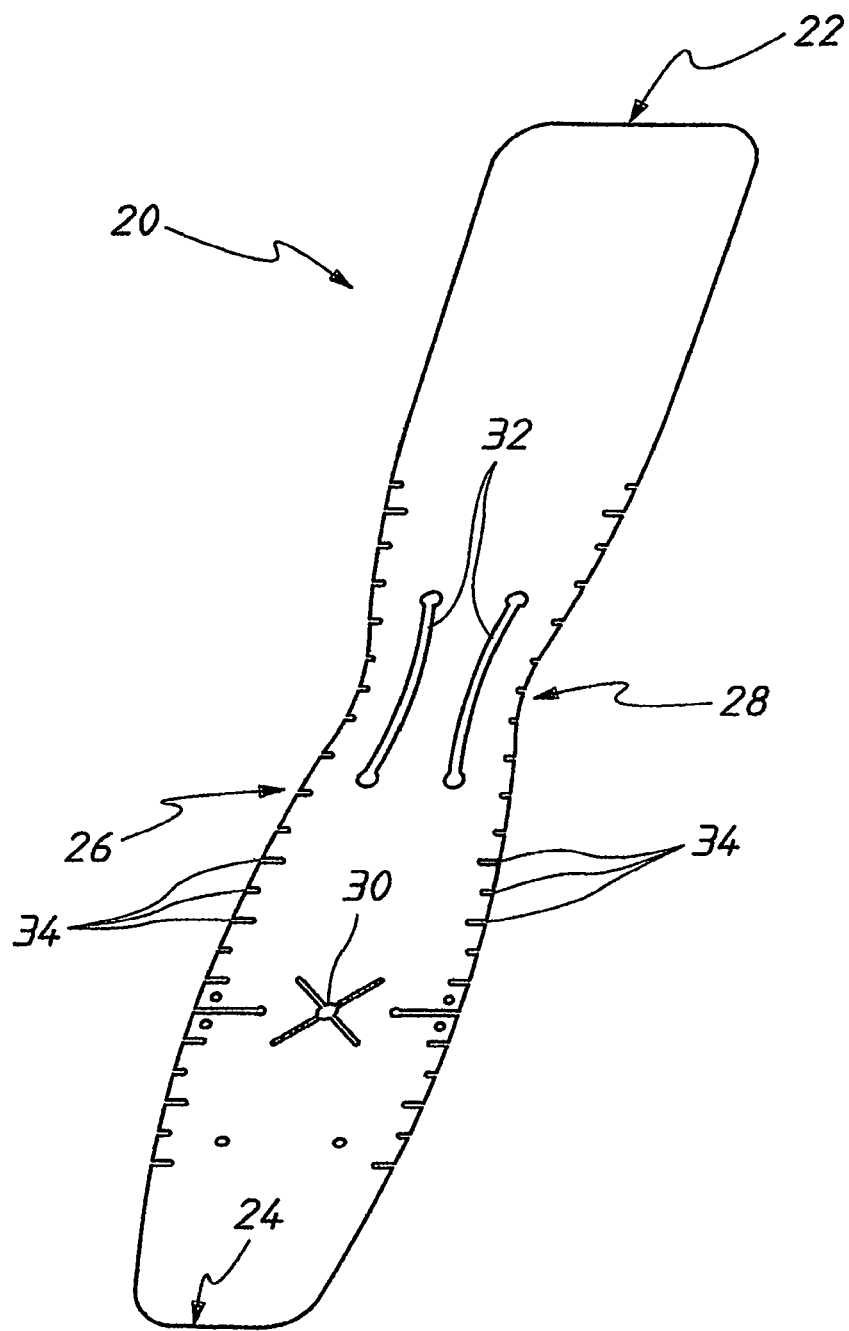
FIG. 2 is a perspective view of the wrap shown in FIG. 1.

Referring firstly to FIGS. 1 and 2, there is shown a wrap 20 according to a first embodiment of the invention. The wrap 20 is produced from woven polyester or similar non-absorbable biostable and biocompatible material and includes ends 22, 24 and sides 26, 28.

The wrap 20 includes an opening 30 for a fluid tube to be connected to, for example, the inflatable balloon or chamber (not shown) of a heart assist device. The wrap 20 also includes a thinned region with a pair of curved longitudinal slits 32, which serve to prevent the wrap from kinking or folding when it is wrapped around a curved portion of aorta.

Figure 3:
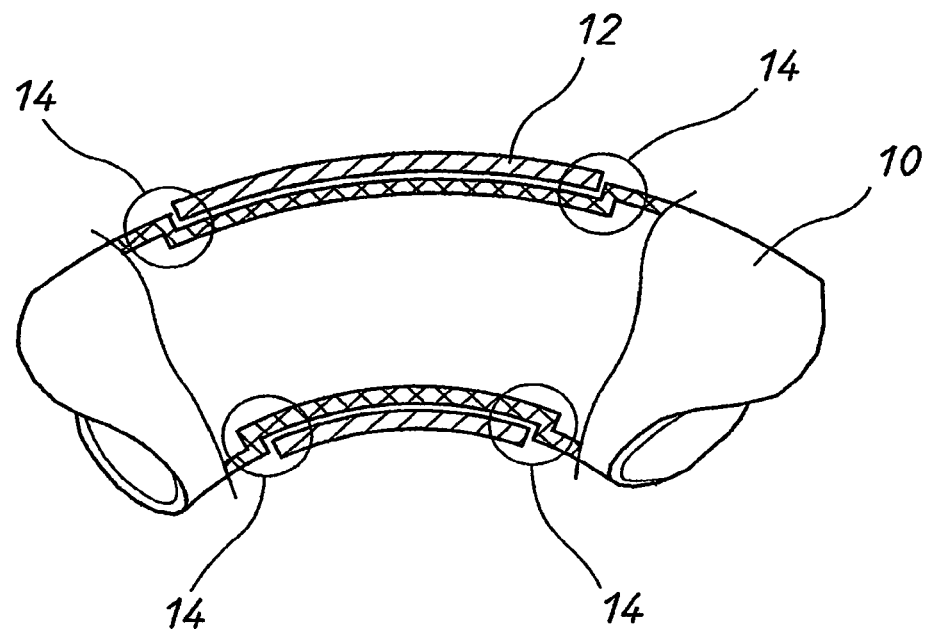
FIG. 3 is a schematic cross-sectional view of a prior art wrap around an aorta.

About two-thirds of the sides 26, 28 of the wrap 20 include a series of spaced apart slits 34 which are substantially normal to the longitudinal axis of the wrap 20. These slits 34 results in those parts of the sides 26, 28 of the wrap 20 being more elastic or stretchable than the intermediate central portion of the wrap 20. As a result, when the wrap 20 is placed around a section of aorta and tightened to a snug fit, less tension is placed in the sides 26, 28 or edges of the wrap 20 than in the centre. This avoids the depression/kinking, and associated high strain levels, associated with known wraps (as was discussed in relation to FIG. 3).

Figure 4:
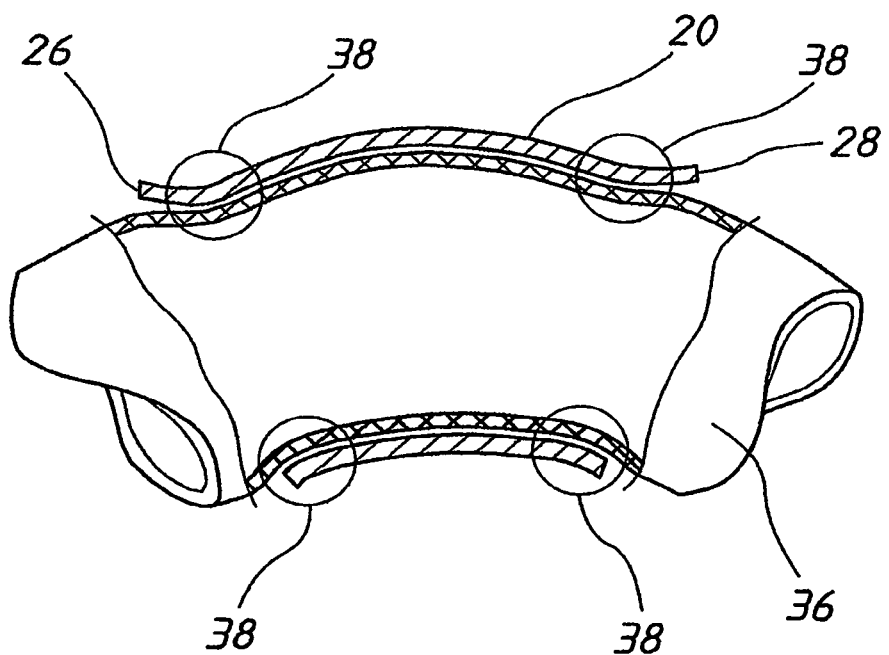
FIG. 4 is a schematic cross-sectional view of the wrap shown in FIG. 1 around an aorta.

A schematic illustration of the wrap 20 around a section of aorta 36 is shown in FIG. 4. The regions 38 of the aorta 36 adjacent the sides 26, 28 of the wrap have a smooth curved transition from a larger to smaller diameter. These curved transition regions 38 result in less strain in the wall of the aorta 36, which reduces the chance of damage to same. The curved transition zones 38 also reduce turbulence in the blood flow through the aorta 36 and thereby reduce the likelihood of plaque formation.

Figure 5:
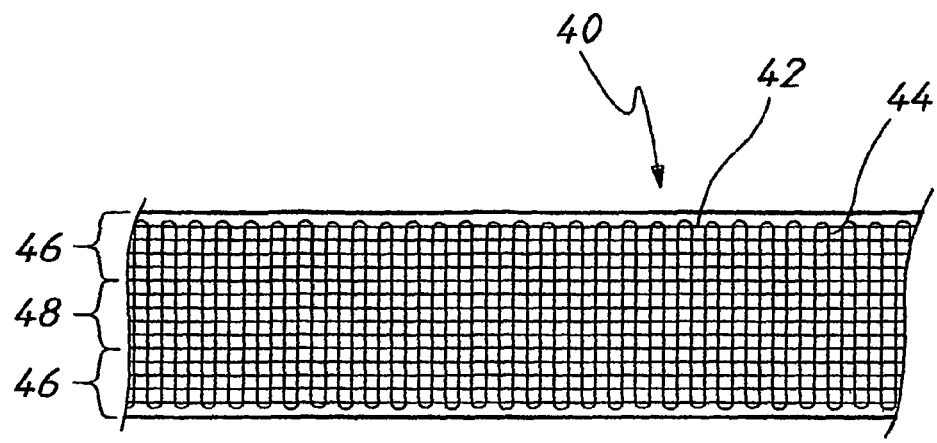
FIG. 5 is a partial top view of a second embodiment of a wrap according to the invention.

A second embodiment of wrap 40 is shown in FIG. 5. In this embodiment, the wrap 40 according to the invention is again of woven polyester construction with longitudinal warp fibres 42 and lateral weft fibres 44. In the wrap 40, the warp fibres 46 adjacent the sides of the wrap 40 are made crimped which makes them more elastic or stretchable than the un-crimped warp fibres 48 in the centre of the wrap 40.

Figure 6:
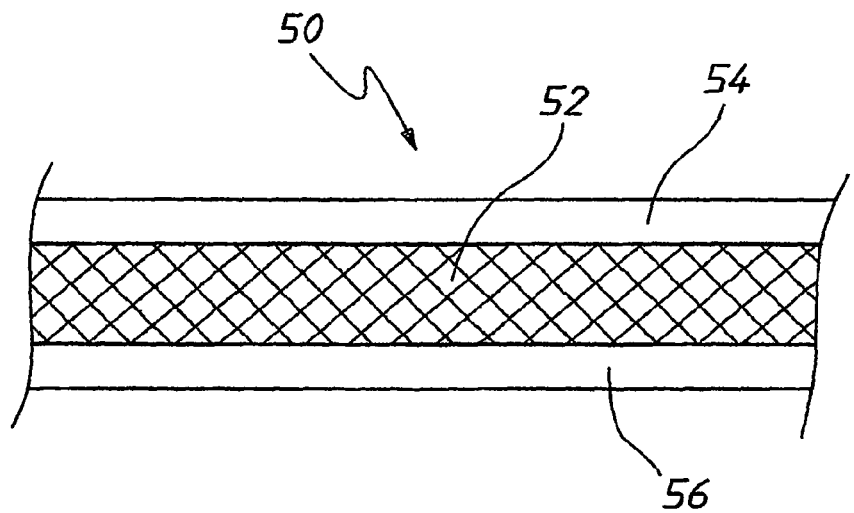
FIG. 6 is a partial top view of a third embodiment according to the invention.

FIG. 6 shows another embodiment of wrap 50 according to the invention which is again of woven polyester construction. The wrap 50 includes a second polyester strip 52 attached to its centre. The strip 52 has a tensile strength greater than that of the rest of the wrap 50 which results in the sides 54, 56 being more elastic or stretchable than the centre 52.

It will be appreciated by persons skilled in the art that numerous variations and/or modifications can be made to the invention as shown in the specific embodiments without departing from the spirit or scope of the invention as broadly defined.

What is claimed is:

1. A wrap for securing about a blood vessel by encasing a section of the vessel, the wrap being of thin flexible construction having two ends and two sides, wherein the wrap is more elastic or stretchable at, near, or along at least one of the two sides compared to at, near, or along its center, to provide strain relief from wrapped to unwrapped aorta.

2. The wrap of claim 1, in combination with an implantable counter-pulsation heart assist device comprising a vessel deformation device.

3. The wrap of claim 1, in combination with a blood vessel deformation device, the wrap being adapted to sandwich the deformation device between the vessel and the wrap.

4. The wrap of claim 3, wherein the vessel deformation device is part of an implantable counter-pulsation heart assist device.

5. The wrap of claim 4, wherein the vessel deformation device is an inflatable balloon or chamber.

6. The wrap of claim 5, wherein the wrap is adapted to secure the inflatable balloon or chamber against an aorta.

7. The wrap of claim 6, wherein the wrap is adapted to secure the inflatable balloon or chamber against an ascending aorta.

8. The wrap of claim 1, wherein the wrap comprises woven or knitted construction, or a combination of those constructions.

9. The wrap of claim 1, wherein the wrap comprises polyester.

10. The wrap of claim 9, wherein the polyester comprises polyethylene terephthalate.

11. The wrap of claim 1, wherein the wrap has slits along a portion of each of the two sides.

12. The wrap of claim 11, wherein the slits comprise a series of spaced apart slits that are normal to the direction of the two sides.

13. The wrap of claim 1, wherein the wrap comprises fibers at, near, or along the two sides that are more elastic than fibers at, near, or along the center of the wrap.

14. The wrap of claim 13, wherein the fibers at, near, or along the two sides are crimped and the fibers at, near, or along the center are un-crimped or less crimped.

15. The wrap of claim 1, wherein the wrap comprises a strip of substantially centrally placed material, the strip comprising a tensile strength greater than that of the rest of the wrap.

16. The wrap of claim 15, wherein the two sides of the wrap are similar, or differing, in elasticity or stretchability to each other.

17. The wrap of claim 1, wherein the wrap comprises woven fabric cut on the bias, wherein the woven fabric is more elastic at or near the two sides.

18. The wrap of claim 1, wherein the wrap is thinner at, near, or along the two sides compared to at, near, or along the center of the wrap.

19. The wrap of claim 1, wherein the wrap is about six times longer than it is wide.

20. The wrap of claim 1, wherein the wrap has a slimmed region at or near a longitudinal midpoint of the wrap.

* * * * *